(12) United States Patent
Wasdyke et al.

(10) Patent No.: US 10,786,267 B2
(45) Date of Patent: Sep. 29, 2020

(54) SHOCKWAVE GENERATING DEVICE

(71) Applicant: Boston Scientific Scimed, Inc., Maple Grove, MN (US)

(72) Inventors: Joel M. Wasdyke, Eden Prairie, MN (US); Daniel James Horn, Shoreview, MN (US); Aaron Lomicka, Edina, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 257 days.

(21) Appl. No.: 16/045,180

(22) Filed: Jul. 25, 2018

(65) Prior Publication Data

US 2019/0029703 A1 Jan. 31, 2019

Related U.S. Application Data

(60) Provisional application No. 62/537,126, filed on Jul. 26, 2017.

(51) Int. Cl.
*A61B 17/22* (2006.01)

(52) U.S. Cl.
CPC ............... *A61B 17/22022* (2013.01); *A61B 2017/22001* (2013.01); *A61B 2017/22021* (2013.01); *A61B 2017/22025* (2013.01); *A61B 2017/22051* (2013.01); *A61B 2017/22061* (2013.01); *A61B 2017/22062* (2013.01)

(58) Field of Classification Search
CPC .......... A61B 17/22022; A61B 17/2202; A61B 2017/22051; A61B 2017/22001; A61B 2017/22021; A61B 2017/22025; A61B 2017/22061; A61B 2017/22062; A61B 2017/22069

See application file for complete search history.

(56) References Cited

U.S. PATENT DOCUMENTS

| | | | |
|---|---|---|---|
| 5,609,606 | A | 3/1997 | O'Boyle |
| 5,611,807 | A | 3/1997 | O'Boyle |
| 6,123,923 | A | 9/2000 | Unger |
| 8,574,247 | B2 | 11/2013 | Adams et al. |
| 8,728,091 | B2 | 5/2014 | Hakala et al. |
| 8,747,416 | B2 | 6/2014 | Hakala et al. |
| 8,888,788 | B2 | 11/2014 | Hakala et al. |
| 8,956,371 | B2 | 2/2015 | Hawkins et al. |
| 9,011,463 | B2 | 4/2015 | Adams et al. |
| 9,044,619 | B2 | 6/2015 | Hawkins et al. |
| 9,138,249 | B2 | 9/2015 | Adams et al. |
| 9,180,280 | B2 | 11/2015 | Hawkins et al. |

(Continued)

FOREIGN PATENT DOCUMENTS

| | | |
|---|---|---|
| GB | 1082397 | 9/1967 |
| WO | 2014025397 | 2/2014 |

OTHER PUBLICATIONS

"Communication Pursuant to Article 94(3) EPC," for European Patent Application No. 18185152.8 dated Jan. 16, 2019 (6 pages).

(Continued)

*Primary Examiner* — Anh T Dang
(74) *Attorney, Agent, or Firm* — Roeder & Broder LLP; James P. Broder (57) ABSTRACT

The present disclosure pertains to assemblies, devices and systems for shockwave generation and to methods of using the same.

17 Claims, 7 Drawing Sheets

(56) References Cited

U.S. PATENT DOCUMENTS

| | | |
|---|---|---|
| 9,220,521 B2 | 12/2015 | Hawkins et al. |
| 9,237,984 B2 | 1/2016 | Hawkins et al. |
| 9,433,428 B2 | 9/2016 | Hakala et al. |
| 9,510,887 B2 | 12/2016 | Burnett |
| 9,554,815 B2 | 1/2017 | Adams |
| 2007/0060990 A1 | 3/2007 | Satake |
| 2007/0270897 A1* | 11/2007 | Skerven ............. A61B 1/00082 606/192 |
| 2009/0247945 A1* | 10/2009 | Levit ................. A61M 25/1002 604/103 |
| 2009/0312768 A1 | 12/2009 | Hawkins et al. |
| 2010/0114065 A1 | 5/2010 | Hawkins |
| 2013/0253466 A1 | 9/2013 | Campbell |
| 2014/0005576 A1 | 1/2014 | Adams et al. |
| 2014/0039002 A1 | 2/2014 | Diodone et al. |
| 2014/0039513 A1* | 2/2014 | Hakala ............... A61B 17/2202 606/128 |
| 2014/0276573 A1* | 9/2014 | Miesel ............... A61B 17/3417 604/506 |
| 2015/0005576 A1 | 1/2015 | Belson et al. |
| 2015/0039002 A1 | 2/2015 | Hawkins |
| 2015/0073430 A1 | 3/2015 | Hakala et al. |
| 2015/0320432 A1 | 11/2015 | Adams |
| 2016/0135828 A1 | 5/2016 | Hawkins et al. |

OTHER PUBLICATIONS

"European Search Report," for European Patent Application No. 18185152.8 dated Dec. 20, 2018 (4 pages).

"NL Search Report and Written Opinion," for Application No. NL2019807 dated Jun. 22, 2018 (10 pages).

* cited by examiner

SHOCKWAVE GENERATING DEVICE

This application claims the benefit of Netherlands Patent Application No. N2019807, filed Oct. 26, 2017 and U.S. Provisional Application No. 62/537,126, filed Jul. 26, 2017, the contents of which are herein incorporated by reference in their entirety.

BACKGROUND

Angioplasty balloons are commonly used to open calcified lesions in the walls of blood vessels. However, as an angioplasty balloon is inflated to expand the lesion in the vascular wall, the inflation pressure stores a tremendous amount of energy in the balloon until the calcified lesion breaks or cracks. That stored energy is then released and may stress and injure the wall of the blood vessel.

Electrohydraulic lithotripsy has been used for breaking calcified lesions in the vasculature. Shockwaves generated by lithotripsy electrodes may be used to fracture a calcified lesion to help prevent sudden stress and injury to a blood vessel or valve wall when it is dilated using a balloon. Methods, devices, system for treating stenotic or calcified vessels or calcified aortic valves are described, for example in U.S. Patent Pub. No. 2009/0312768, U.S. Patent Pub. No. 2014/0005576, and U.S. Pat. No. 8,888,788. As described in those applications, a balloon is placed adjacent a treatment site and is inflated with a liquid. Within the balloon is a shockwave generator that produces shockwaves that propagate through the liquid and impinge upon the target tissue prior to balloon expansion.

There is a continuing need in the art for improved shockwave generating device designs and for shockwave generating devices that can improve deliverability to treatment sites and be readily manufactured at low cost.

BRIEF SUMMARY

Described herein are low-profile electrode assemblies which may be used, for example, in conjunction with shockwave angioplasty balloon catheters. Such devices may, for instance, be used to break up calcified lesions in the vasculature.

In accordance with various aspects, the present disclosure pertains to devices for generating shockwaves, the devices comprising: (a) an inner electrode assembly comprising an inner elongate member, an inner conductive layer disposed over the inner elongate member, an insulating layer disposed over the inner conductive layer, an outer conductive layer disposed over the insulating layer, and a multilayer aperture that comprises a first aperture extending through the insulating layer and a second aperture extending through the outer conductive layer, wherein the first aperture and the second aperture are coaxial with one another, and wherein the multi-layer aperture (i) exposes a portion of an upper surface of the inner conductive layer at a bottom of the multi-layer aperture, which corresponds to a first electrode and (ii) exposes at least a lateral surface of the outer conductive layer surrounding the multi-layer aperture, which corresponds to a second electrode, (b) a balloon, wherein the multi-layer aperture of the inner electrode assembly is positioned inside the balloon, and (c) an elongate shaft comprising a lumen that is configured to introduce conductive fluid into the balloon.

In some embodiments, which can be used in conjunction with the above aspects, a width of the first aperture is the same as a width of the second aperture.

In some embodiments, which can be used in conjunction with the above aspects, a width of the first aperture is different from a width of the second aperture, in which case a width of the first aperture may be smaller than a width of the second aperture, or a width of the first aperture may be greater than a width of the second aperture.

In some embodiments, which can be used in conjunction with any of the above aspects and embodiments, the device may comprise a plurality of the multi-layer apertures. In certain of these embodiments, at least some of the plurality of the multi-layer apertures are circumferentially offset from each other. For example, the plurality of the multi-layer apertures may comprise (a) two multi-layer apertures that are circumferentially offset from one another by an angle of 180°, (b) three multi-layer apertures that are circumferentially offset from one another by an angle of 120°, (c) four multi-layer apertures that are circumferentially offset from one another by an angle of 90°, (d) five multi-layer apertures that are circumferentially offset from one another by an angle of 72°, (e) six multi-layer apertures that are circumferentially offset from one another by an angle of 60°, or (f) eight multi-layer apertures that are circumferentially offset from one another by an angle of 45°, among other possibilities. In certain of these embodiments, at least some of the plurality of the multi-layer apertures are longitudinally offset from each other. In certain of these embodiments, at least some of the plurality of the multi-layer apertures are both circumferentially and longitudinally offset from each other.

In some embodiments, which can be used in conjunction with any of the above aspects and embodiments, the device may further comprise an additional insulating layer disposed over at least a portion of the outer conductive layer. In these embodiments, the multi-layer aperture may comprise a third aperture formed in the additional insulating layer, which third aperture may or may not be coaxial with the first aperture and the second aperture.

In some embodiments, which can be used in conjunction with any of the above aspects and embodiments, a proximal end of the balloon may be attached to a distal end of the elongate shaft, and a distal end of the balloon may be attached to a distal end of the inner electrode assembly.

In some embodiments, which can be used in conjunction with any of the above aspects and embodiments, the inner elongate member may comprise a lumen. In certain of these embodiments, a guidewire may be disposed within the lumen of the inner elongate member.

In other aspects of the present disclosure, systems are provided that comprise: (a) a device for generating shockwaves in accordance with any of the above aspects and embodiments and (b) a voltage generator in electrical connection with the inner and outer conductive layers and configured to apply a voltage pulse across the inner and outer conductive layers that is of sufficient magnitude and duration to generate a shock wave.

In other aspects of the present disclosure, methods of making medical devices for generating shockwaves are provided, the methods comprising forming an inner electrode assembly comprising an inner elongate member, an inner conductive layer disposed over the inner elongate member, an insulating layer disposed over the inner conductive layer, an outer conductive layer disposed over the insulating layer, and a multilayer aperture that comprises a first aperture extending through the insulating layer and a second aperture extending through the outer conductive layer, wherein the first aperture and the second aperture are coaxial with one another, and wherein the multi-layer aperture exposes (i) a portion of an upper surface of the inner conductive layer at a bottom of the multi-layer aperture, which corresponds to a first electrode and (ii) at least a lateral surface of the outer conductive layer surrounding the multi-layer aperture, which corresponds to a second electrode.

In some embodiments, which can be used in conjunction with any of the above aspects, the method further comprises incorporating the inner electrode assembly into a balloon catheter that comprises a balloon and an elongate shaft comprising a lumen that is configured to introduce conductive fluid into the balloon, such that the multi-layer aperture of the inner electrode assembly is positioned inside the balloon.

In some embodiments, which can be used in conjunction with any of the above aspects and embodiments, forming the inner electrode assembly may comprise: (a) inserting a first subassembly into a second subassembly, the first subassembly comprising the inner elongate member and the inner conductive layer disposed over the inner elongate member, and the second subassembly comprising the insulating layer, the outer conductive layer disposed over the insulating layer, the first aperture extending through the insulating layer, and the second aperture extending through the outer conductive layer; and (b) affixing the first subassembly to the second subassembly. In certain of these embodiments, the first subassembly may be affixed to the second subassembly by shrinking the second subassembly onto a surface of the first subassembly.

In some embodiments, which can be used in conjunction with any of the above aspects and embodiments, forming the inner electrode assembly comprises forming the multi-layer aperture in an assembly that comprises the inner elongate member, the inner conductive layer disposed over the inner elongate member, the insulating layer disposed over the inner conductive layer, and the outer conductive layer disposed over the insulating layer. In certain of these embodiments, the forming the multi-layer aperture comprises: (i) forming the second aperture in the outer conductive layer by a first process that removes a material of the outer conductive layer, thereby exposing the lateral surface of the outer conductive layer and (ii) forming the first aperture in the insulating layer using a second process that removes a material of the insulating layer, thereby exposing an upper surface of the inner conductive layer. For instance, the first process may be one that selectively removes the material of the outer conductive layer relative to the material of the insulating layer, and the second process may be one that selectively removes the material of the insulating layer relative to a material of the inner conductive layer.

These and other aspects, embodiments and advantages of the present disclosure will become immediately apparent to those of ordinary skill in the art upon review of the detailed description and claims to follow.

DETAILED DESCRIPTION

Described herein are devices and systems that comprise one or more shockwave generators comprising shockwave-generating electrodes. The shockwave generators are integral to an inner electrode assembly, which may be sealed within a balloon that is inflated with a conductive fluid (e.g., saline, imaging contrast agent, etc.). The inner electrode assembly may be attached to a source of high voltage pulses, for example, ranging from 100 to 10,000 volts, more typically 100 to 3,000 volts, for various pulse durations, which, without wishing to be bound by theory, may generate rapidly expanding and collapsing bubbles, which in turn create mechanical shockwaves within the balloon. Shockwaves may be mechanically conducted through the fluid and through a wall of the balloon to apply mechanical stress to break apart calcified lesions that may be present on or in the vasculature walls.

Figure 1:
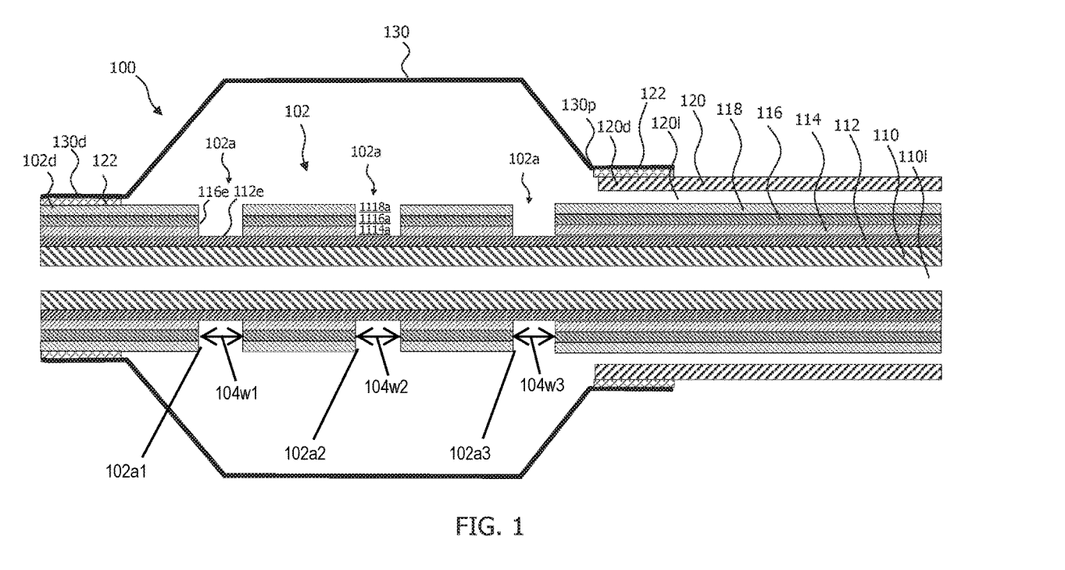
FIG. 1 depicts a schematic cross-sectional view of a shockwave angioplasty device, in accordance with the present disclosure.

FIG. 1 is a schematic illustration of a shockwave angioplasty device 100 in accordance with the present disclosure. The device 100 of FIG. 1 includes an inner electrode assembly 102, an outer tubular member 120, and a balloon 130. The inner electrode assembly 102 includes an inner elongate member 110 (sometimes referred to herein as "elongate member"), an inner conductive layer 112 disposed over the inner elongate member 110, an insulating layer 114 disposed over the inner conductive layer 112, an outer conductive layer 116 disposed over the insulating layer 114, and an optional additional insulating layer 118 disposed over the outer conductive layer 116.

The inner elongate member 110 may be formed from any suitable material, beneficially a low-friction polymeric material such as, for example, polytetrafluoroethylene (PTFE), fluorinated ethylene propylene (FEP), a copolymer of hexafluoropropylene and tetrafluoroethylene, or high-density polyethylene (HDPE), among other possibilities. The inner elongate member 110 may range, for example, from 0.018 to 0.042 inch (0.46 mm to 1.1 mm) in outer diameter, among other possibilities. The inner elongate member 110 may include a guide wire lumen 110l extending along a length of its longitudinal axis. The guide wire lumen 110l may range, for example, from 0.014 to 0.038 inch (0.36 mm to 0.97 mm) in diameter, among other possibilities.

The inner conductive layer 112 and the outer conductive layer 116 may be formed from any material that is able to support the voltages that are required for shockwave generation and to withstand the forces generated by the same. For example, the inner conductive layer 112 and the outer conductive layer 116 may be made of tungsten, nickel, iron, steel, including stainless steel, copper, gold, and the like. The inner conductive layer 112 may range, for example, from 0.000005" to 0.00005" (0.00013 mm to 0.0013 mm) in thickness, among other possibilities. The outer conductive layer 116 may range, for example, from 0.000005" to 0.00005" (0.00013 mm to 0.0013 mm) in thickness, among other possibilities.

The insulating layer 114 may be made of any material having a breakdown voltage that is sufficiently great to withstand voltages that are generated during shockwave generation, for example, fluoropolymers (e.g., PTFE, FEP, etc.), polyethylene terephthalate (PET), polyimide (e.g., Kapton), polyamides, polyamide block polyether copolymers, polyester block copolymers, and the like. As discussed further below, in some embodiments, the insulating layer 114 may be formed from a shrinkable material, for example, a heat-shrinkable material. The insulating layer 114 may range, for example, form 0.0005" to 0.003" (0.01 mm to 0.08 mm) in thickness, among other possibilities.

The optional additional insulating layer 118 may be formed by the same materials as the insulating layer 114, although the electrical demands upon the additional insulating layer 118 may not be as great as those associated with insulating layer 114. The additional insulating layer 118 may range, for example, from 0.0005" to 0.003" (0.01 mm to 0.08 mm) in thickness, among other possibilities.

The inner electrode assembly 102 further includes a plurality of multi-layer apertures 102a (six shown, three of which are labeled), each including a first aperture 1114a extending through the insulating layer 114, a second aperture 1116a extending through the outer conductive layer 116, and a third aperture 1118a extending through the optional additional insulating layer 118. The first aperture 1114a, second aperture 1116a, and third aperture 1118a are preferably coaxial with one another. Within each multi-layer aperture 102a lies an exposed portion of the inner conductive layer 112, which corresponds to an inner electrode 112e. In the embodiment shown, an exposed portion of the outer conductive layer 116 is also contained within each multi-layer aperture 102a, corresponding to an outer electrode 116e. By applying a voltage pulse of suitable magnitude and duration across the inner electrode 112e and outer electrode 116e in the presence of a conductive liquid, microbubble creation and collapse may be initiated in the vicinity of each multi-layer aperture 102a, leading to the creation of a shockwave, which propagates radially outward from the side of the inner electrode assembly 102. Thus, each aperture in FIG. 1 corresponds to a shockwave generator. The inner electrode 112e may be a positive electrode and the outer electrode 116e may be a negative electrode or ground electrode, conversely, the outer electrode 116e may be a positive electrode and the inner electrode 112e may be a negative electrode or ground electrode, and so forth. More broadly, a potential difference is established between the inner electrode 112e and the outer electrode 116e that has a magnitude and duration sufficient for shockwave creation.

The multi-layer apertures 102a (and thus the shockwave generators) may be distributed along a longitudinal length of the elongate member. For example, the multi-layer apertures 102a may be longitudinally spaced by a distance ranging from about 4 mm to 25 mm, among other possible values.

As an alternative or in addition to being distributed along a longitudinal length of the elongate member, the multi-layer apertures 102a may be distributed around a circumference of the elongate member 110. For example, the multi-layer apertures 102a may comprise any of the following: two multi-layer apertures 102a that are circumferentially offset from one another by an angle of 180°, three multi-layer apertures 102a that are circumferentially offset from one another by an angle of 120°, four multi-layer apertures 102a that are circumferentially offset from one another by an angle of 90°, five multi-layer apertures 102a that are circumferentially offset from one another by an angle of 72°, six multi-layer apertures 102a that are circumferentially offset from one another by an angle of 60°, or eight multi-layer apertures 102a that are circumferentially offset from one another by an angle of 45°, among other possibilities.

The first aperture 1114a, a second aperture 1116a and (optional) third aperture 1118a may be in the shape of a circle, oval, ellipse, polygon, or any other desired shape. In addition to the thickness of the insulating layer 114, the nature of the path that the current travels during shockwave formation is influenced by the size and location of the first aperture 1114a in the insulating layer 114 and the size and location of the second aperture 1116a in the outer conductive layer 116. The first aperture 1114a in the insulating layer 114 may be the same size as the second aperture 1116a in the outer conductive layer 116, or may be smaller than the second aperture 1116a in the outer conductive layer 116. The third aperture 1118a in the optional additional insulating layer 118 may be may be the same size as the second aperture 1116a in the outer conductive layer 116 or may be larger than the second aperture 1116a in the outer conductive layer 116.

In certain beneficial embodiments, the first aperture 1114a in the insulating layer 114 may have a diameter ranging from 0.019" to 0.043" (0.48 mm to 1.09 mm), among other possible values, the second aperture 1116a in the outer conductive layer 116 may have a diameter ranging from 0.020" to 0.044" (0.51 mm to 1.12 mm), among other possible values, and the third aperture 1118a in the optional additional insulating layer 118 may have a diameter ranging from 0.021" to 0.045" (0.53 mm to 1.14 mm), among other possible values. The ratio of the diameters between the first aperture 1114a, the second aperture 1116a, and the third aperture 1118a may be varied to change the nature of the generated shockwave.

In some embodiments, the widths of one or more of the first apertures 1114a second apertures 1116a and optional third apertures 1118a may vary along a longitudinal length of the inner electrode assembly 102. For example, aperture widths may be varied along the longitudinal length of the inner electrode assembly 102 such that shockwave generators at the proximal and distal ends of the array deliver higher power shockwaves than those delivered at the center of the array.

The inner electrode assembly 102 may be used in conjunction with an axially extending catheter that further includes a balloon 130 and an outer tubular member 120. The multi-layer apertures 102a (and thus the shockwave generators) of the inner electrode assembly 102 are positioned within the balloon 130. A proximal end 130p of the balloon 130 is attached to a distal end 120d of the outer tubular member 120, and a distal end 130d of the balloon 130 is attached to the distal end 102d of the inner electrode assembly 102. Although the layers 112, 114, 116, 118 are shown extending proximally beyond the proximal end 130p of the balloon 130, this is not required. For example, electrical leads can be provided, which extend the length of the catheter and connect the inner and outer conductive layers 112, 116 to a suitable voltage source.

The balloon 130 may be a single layer or multi-layer balloon formed of any suitable material, including polyethylene terephthalate (PET), polyether block amide (e.g., PEBAX), polyamide (e.g., nylon), polyethylene, polyurethane, silicone, and other materials known in the medical balloon art. The balloon 130 may be attached to the outer tubular member 120 and the inner electrode assembly 102 using any method known in the balloon art, including, for example, a suitable adhesive 122. In the embodiment shown, conductive fluid may be introduced into and removed from the balloon 130 through a lumen 120l that lies between the inner electrode assembly 102 and the outer tubular member 120.

In this regard, it is noted that devices in accordance with the present disclosure can be used in conjunction with standard balloon manufacturing methods, except that the inner is in the form of an inner electrode assembly 102, which is constructed so that there are multiple locations in which multi-layer apertures 102a are provided, which correspond to shockwave generators. In this regard, when filled with a conductive fluid, the multi-layer apertures 102a provide electrical pathways between the inner and outer conductive layers 112, 116, such that a voltage generator can be used to apply a voltage across the inner and outer conductive layers 112, 116 that is of suitable magnitude and duration for shockwave generation. The shockwave generators are integral to the inner electrode assembly 102. The voltage generator is connected to the inner and outer conductive layers 112, 116 of the inner electrode assembly 102, and applies a suitable voltage across the inner and outer conductive layers 112, 116. In some embodiments, leads can be extended along the inner member 110, which are attached to the inner and outer conductive layers 112, 116 proximate the proximal end of the balloon 130. The leads may also be connected to a voltage generator.

Without wishing to be bound by theory, applying a voltage across the inner and outer conductive layers 112, 116, can create high temperature zones in the vicinity of the apertures 102a, which in turn creates micro bubbles of steam. The creation and collapse of the bubbles creates shockwaves which radiate outward from the inner electrode assembly 102. These shockwaves may be used, for example, to disrupt hard calcified lesions in a vessel surrounding the balloon 130, making is easier for the balloon 130 to expand the vessel. The lower pressure required for expansion typically creates a better clinical outcome than POBA (plain old balloon angioplasty). In addition, the breakup of calcified lesions may provide channels for improved uptake of drug from a drug coated balloon.

Shockwave intensity may be controlled in various ways including, for example, by controlling the width of the first apertures 1114a, second apertures 1114a and third apertures 1118a within the multi-layer apertures 102a, by controlling the thickness of the insulating layer 114, by controlling the number of multi-layer apertures 102a (and thus the number of shockwave generators), and by controlling the magnitude and duration of the voltage that is applied by the voltage generator to the inner and outer conductive layers 112, 116.

Other aspects of the present disclosure pertain to methods of making medical devices for generating shockwaves. The methods include forming inner electrode assemblies 102 like those described above, in particular, inner electrode assemblies 102 that comprise an inner elongate member 110, an inner conductive layer 112 disposed over the inner elongate member 110, an insulating layer 114 disposed over the inner conductive layer 112, an outer conductive layer 116 disposed over the insulating layer 114, an optional additional insulating layer 118 disposed over the outer conductive layer 116, and one or more multi-layer apertures 102a extending from an outer surface of the inner electrode assembly 102 down to the inner conductive layer 112 of the inner electrode assembly 102, each multi-layer aperture 102a corresponding to a shockwave generator.

Figure 2A:
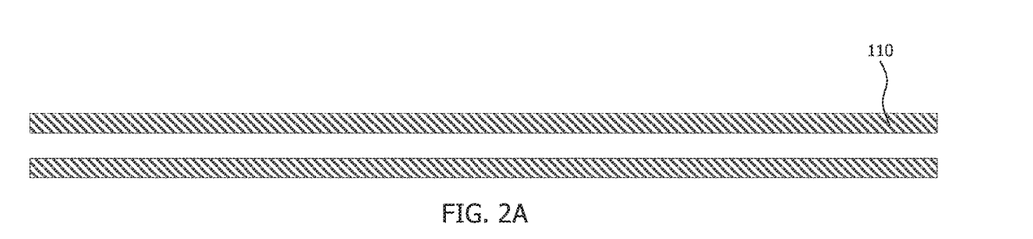
FIGS. 2A-2B are schematic cross-sectional views illustrating a process for forming a first subassembly, in accordance with the present disclosure.

In some embodiments, for example, a first subassembly is inserted into a second subassembly, and the first and second subassemblies are then affixed to one another. For example, and with reference to FIGS. 2A-2B, a first subassembly 102s1 may be formed by taking an elongate member 110 as shown in FIG. 2A and forming a conductive layer 112 on the elongate member 110 using any suitable method, for example, by depositing a conductive layer 112 on an elongate member 110 using a suitable process, such as physical vapor deposition process, a chemical vapor deposition process, or an electroplating process, or by wrapping a conductive layer 112 around an elongate member 110. In one specific embodiment, a metal conductive layer 112 may be sputter deposited on an elongate member 110 in the form of a PTFE tube.

Figure 3A:
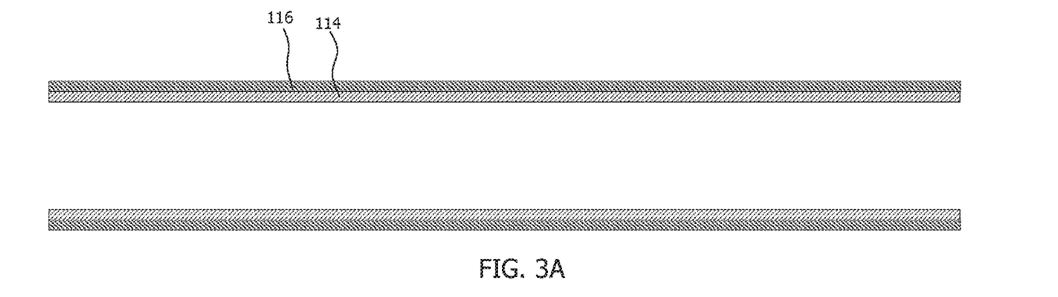
FIGS. 3A-3B are schematic cross-sectional views illustrating a process for forming a second subassembly, in accordance with the present disclosure.

Referring now to FIGS. 3A-3B, a second subassembly 102s2 may be formed by first creating a tubular member that comprises an insulating layer 114 and a conductive layer 116 like that shown in FIG. 3A (as well as an optional additional insulating layer, not shown). For example, using any suitable layer formation method, a conductive layer 116 may be formed on an outer surface of an insulating layer 114 in the form of a tube of insulating material. For instance, a conductive layer 116 may be deposited on an insulating layer 114 in form of a tube of insulating material using a suitable deposition process, such as a physical vapor deposition process, a chemical vapor deposition process, or an electroplating process. In one particular embodiment, a layer of conductive material may be applied to a heat-shrinkable tube of insulating material, for example, a heat-shrinkable FEP tube, a heat-shrinkable PET tube, or nylon, polyolefins, among other possibilities.

Figure 3B:
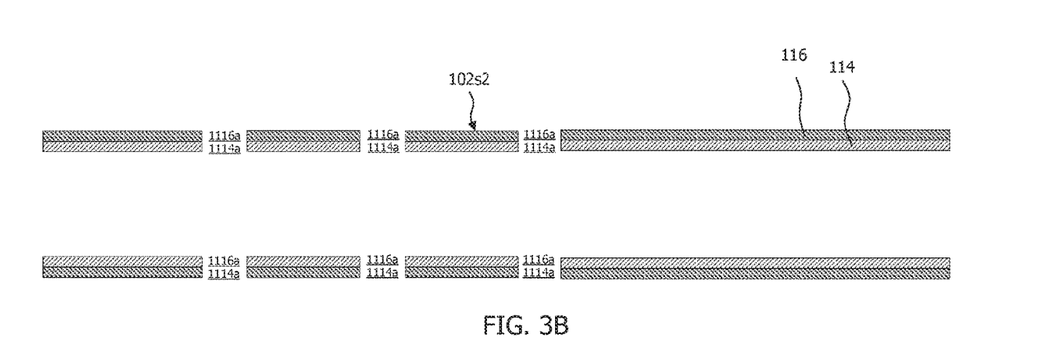

Subsequently, apertures 1114a, 1116a may be formed in the tubular member 114, 116 using a suitable physical, chemical, or physicochemical process, such as, for example, mechanical drilling, laser drilling, or masking and etching, among other processes, thereby completing the second subassembly 102s2.

Figure 2B:
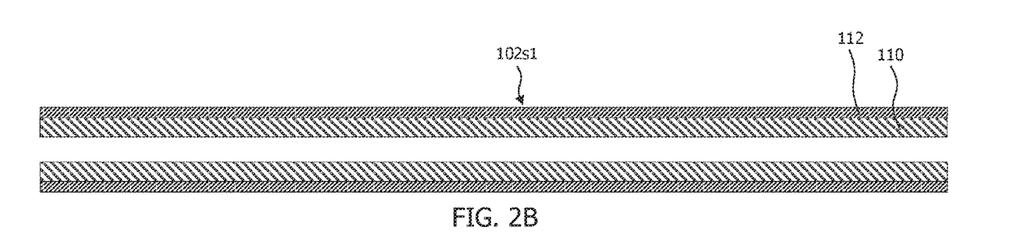
Figure 4A:
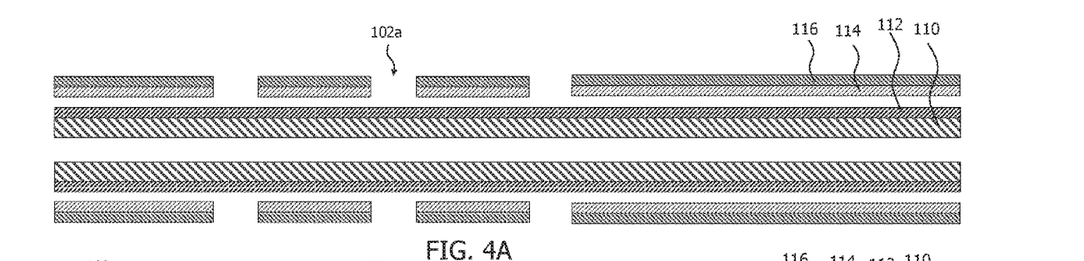
FIGS. 4A-4B are schematic cross-sectional views illustrating a process for forming an inner electrode assembly, in accordance with the present disclosure.
Figure 4B:
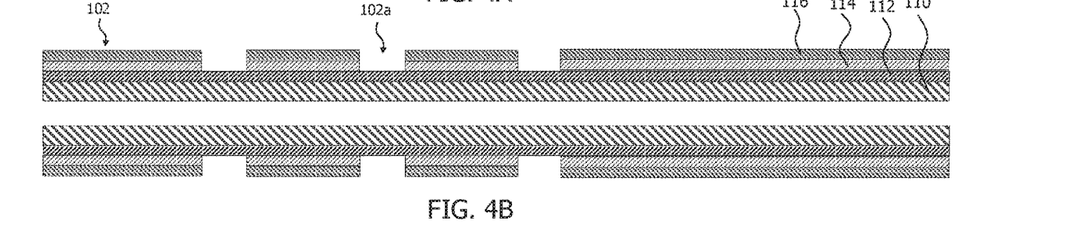
Figure 5:
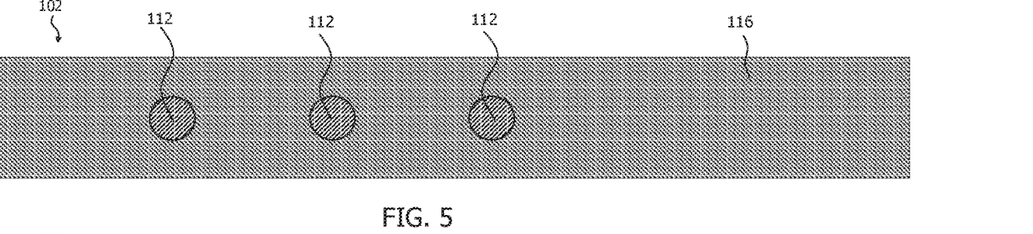
FIGS. 5 and 6 are schematic side views illustrating inner electrode assemblies, in accordance with the present disclosure.
Figure 6:
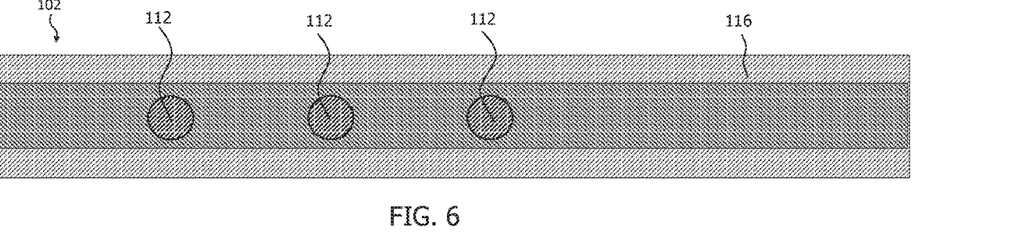

In a subsequent step, the first subassembly 102s1 of FIG. 2B is positioned inside the second subassembly 102s2 of FIG. 3B to form an assembly like that shown in FIG. 4A. Subsequently, the second subassembly 102s2 is shrunk onto the first subassembly 102s1, for example, via heat shrinking or another suitable process, thereby forming an inner subassembly 102 as shown in FIG. 4B. A side view of the inner assembly 102 of FIG. 4B is shown in FIG. 5. To enhance the shrinkage process, in some embodiments, the outer conductive layer 116 in the second subassembly 102s2 may be provided over only a portion of the surface of the second subassembly 102s2. For example, the outer conductive layer 116 may be present as a series of conductive lines as shown in FIG. 6, or more complex patterns may be employed such as barber-pole and zig-zag patterns (see also, for example, FIG. 8, discussed further below).

Figure 7A:
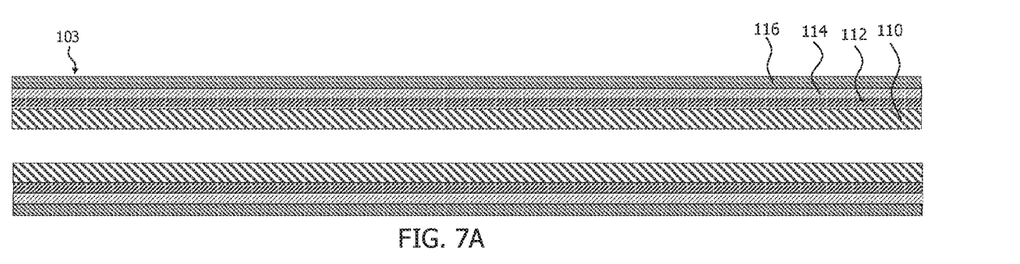
FIGS. 7A-7B are schematic cross-sectional views illustrating a process for forming an inner electrode assembly, in accordance with the present disclosure.
Figure 7B:
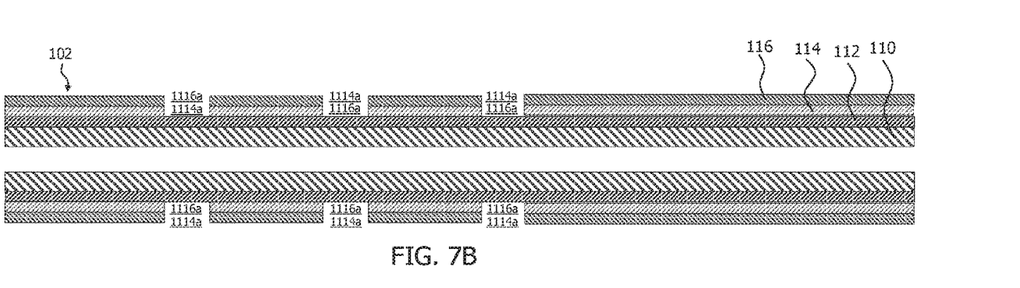

In some embodiments, an inner electrode assembly 102 like that shown in FIG. 7B is created by forming apertures 102a in an assembly 103 like that shown in FIG. 7A, which includes an inner elongate member 110, an inner conductive layer 112 disposed over the inner elongate member 110, an insulating layer 114 disposed over the inner conductive layer 112, an outer conductive layer 116 disposed over the insulating layer 114, and optionally an additional insulating layer (not shown). The apertures may be formed, for example, using any suitable physical, chemical, or physicochemical process, such as mechanical drilling, laser drilling, or masking and etching processes, among others.

In some instances, a process may be selected in which apertures are formed using a process that selectively removes material making up a given layer, relative to another material making up an underlying layer. For example, a process may be selected in which conductive material in the outer conductive layer 116 is selectively removed relative to insulating material in the insulating layer 114 underlying the outer conductive layer 116, such that the insulating layer 114 acts as a stop layer when apertures 1116a are formed in the outer conductive layer 116. For instance, a process may be selected which removes conductive material from the outer conductive layer 116 at a rate that is at least two times, more beneficially at least four times, even more beneficially at least ten times, the rate at which the process removes insulating material from insulating layer 114.

After forming apertures 1116a, another process may be selected in which insulating material in the insulating layer 114 is selectively removed relative to conductive material in the inner conductive layer 112 underlying the insulating layer 114, such that the inner conductive layer 112 acts as a stop layer when apertures 1114a are formed in the insulating layer 114. For instance, a process may be selected which removes insulating material from the insulating layer 114 at a rate that is at least two times, more beneficially at least four times, even more beneficially at least ten times the rate at which that process removes conductive material from the inner conductive layer 112.

As a specific example, metallic material may be selectively removed from the outer conductive layer 116 (relative to material in the insulating layer 114) using an excimer laser or using a suitable plasma etching chemistry, whereas insulating material may be selectively removed from the insulating layer 114 (relative to the inner conductive layer 112) using a $CO_2$ laser or a excimer laser or using a suitable plasma etching chemistry. Plasma etching chemistries in which insulating materials (e.g., fluoropolymers) are selectively etched relative to conductive materials (e.g., metals), and in which conductive materials are selectively etched relative to insulating materials, are known in the semiconductor processing industry.

Figure 8A:
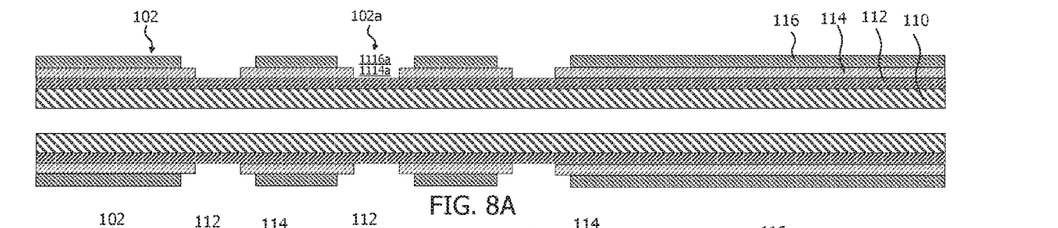
FIGS. 8A and 8B are schematic cross-sectional and side views, respectively, illustrating an inner electrode assembly, in accordance with the present disclosure.
Figure 8B:
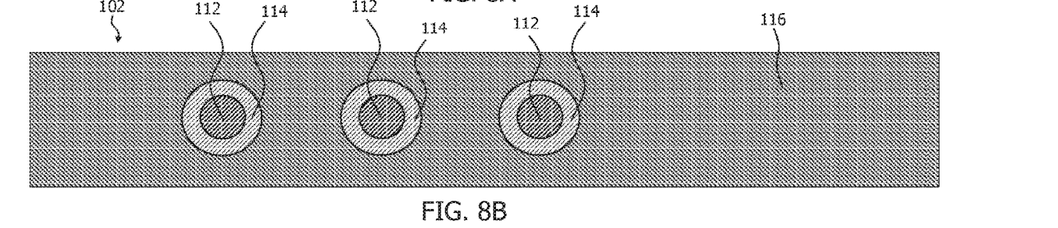
Figure 9:
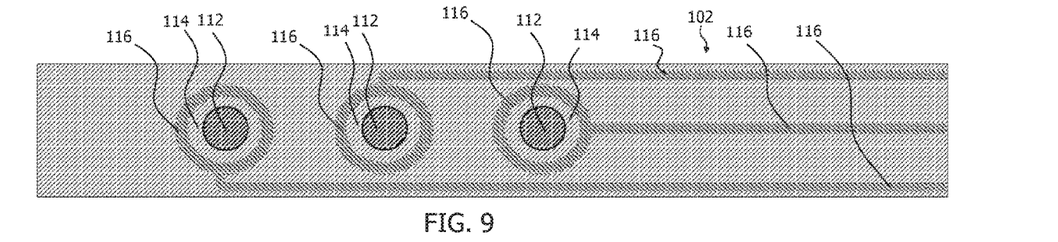
FIG. 9 is schematic side view illustrating an inner electrode assembly, in accordance with the present disclosure.

Using these and other processes, a wide range of aperture sizes and layer layouts may be created, one example of which is an inner assembly 102 like that shown in schematic cross-sectional and side views in FIGS. 8A and 8B, another of which is an inner assembly 102 like that shown in schematic side view in FIG. 9.

Although various embodiments are specifically illustrated and described herein, it will be appreciated that modifications and variations of the present disclosure are covered by the above teachings and are within the purview of the appended claims without departing from the spirit and intended scope of the disclosure.

The invention claimed is:

1. A device for generating shockwaves, the device comprising:
   an elongate member having a distal portion;
   an outer tubular member that is disposed around the elongate member so that a lumen is formed between the elongate member and the outer tubular member;
   a balloon that is disposed on the distal portion of the elongate member, the balloon being configured to receive a conductive fluid via the lumen;
   an inner electrode assembly including (i) an inner conductive layer disposed over the distal portion of the elongate member, (ii) an insulating layer disposed over the inner conductive layer, and (iii) an outer conductive layer disposed over the insulating layer, the inner electrode assembly having a multi-layer aperture that extends through the insulating layer and the outer conductive layer to expose a portion of the inner conductive layer and a portion of the outer conductive layer; and
   an additional insulating layer that is disposed over at least a portion of the outer conductive layer;
   wherein the multi-layer aperture includes a first aperture that extends through the insulating layer, a second aperture that extends through the outer conductive layer, and a third aperture that extends through the additional insulating layer, the third aperture being coaxial with the first aperture and the second aperture.

2. The device of claim 1, wherein a width of the first aperture is smaller than a width of the second aperture.

3. The device of claim 1, further comprising a plurality of the multi-layer apertures that are disposed on the inner electrode assembly.

4. The device of claim 3, wherein at least two of the plurality of the multi-layer apertures are circumferentially offset from each other.

5. The device of claim 3, wherein the plurality of the multi-layer apertures comprises a distribution pattern selected from at least one of the group consisting of (a) two of the multi-layer apertures that are circumferentially offset from one another by an angle of 180°, (b) three of the multi-layer apertures that are circumferentially offset from one another by an angle of 120°, (c) four of the multi-layer apertures that are circumferentially offset from one another by an angle of 90°, (d) five of the multi-layer apertures that are circumferentially offset from one another by an angle of 72°, (e) six of the multi-layer apertures that are circumferentially offset from one another by an angle of 60°, and (f) eight of the multi-layer apertures that are circumferentially offset from one another by an angle of 45°.

6. The device of claim 3, wherein some of the plurality of the multi-layer apertures are longitudinally offset from each other.

7. The device of claim 1, wherein the balloon has a first end attached to the distal end of the outer tubular member and a second end attached to the distal end of the inner electrode assembly.

8. The device of claim 1, wherein the elongate member further comprises a guide wire lumen.

9. The device of claim 1, wherein the insulating layer is formed from a shrinkable material.

10. A device for generating shockwaves, the device comprising: a balloon; and an inner electrode assembly that is at least partially positioned within secured to the balloon, the inner electrode assembly including
   (i) an elongate member having a distal end,
   (ii) an inner conductive layer that is disposed over at least a portion of the distal end of the elongate member,
   (iii) an insulating layer that is disposed over the inner conductive layer,
   (iv) a first aperture formed in the insulating layer, the first aperture exposing a portion of the inner conductive layer, and
   (v) an outer conductive layer disposed over the insulating layer with a second aperture extending therethrough, and
   (vi) an additional insulating layer that is disposed over at least the inner electrode assembly, the additional insulating layer having an additional aperture located coaxially with the aperture; the first and second apertures of the inner electrode assembly defining a multi-layer aperture that extends through the insulating layer and the outer conductive layer to expose a portion of the inner conductive layer and a portion of the outer conductive layer.

11. The device of claim 10, wherein the elongate member includes a guide wire lumen.

12. The device of claim 10, further comprising a plurality of multi-layer apertures that are disposed on the inner electrode assembly.

13. The device of claim 12, wherein the plurality of multi-layer apertures are longitudinally offset from each other.

14. The device of claim 12, wherein each of the plurality of multi-layer apertures can be independently activated.

15. The device of claim 10, wherein the inner electrode assembly includes at least three multi-layer apertures.

16. The device of claim 15, further comprising a plurality of the multi-layer apertures that are disposed on the inner electrode assembly.

17. The device of claim 10, wherein the elongate member defines a guide wire lumen.

* * * * *